United States Patent [19]

Anazawa et al.

[11] Patent Number: 5,192,320
[45] Date of Patent: Mar. 9, 1993

[54] ARTIFICIAL LUNG AND METHOD OF USING IT

[75] Inventors: Takanori Anazawa; Kazutaka Murata, both of Sakura; Hiroyuki Akasu; Rishichi Mimura, both of Kurashiki, all of Japan

[73] Assignees: Dainippon Ink and Chemicals Inc., Tokyo; Kuraray Co., Ltd., Okayama, both of Japan

[21] Appl. No.: 488,452

[22] Filed: Feb. 23, 1990

Related U.S. Application Data

[63] Continuation of Ser. No. 216,547, Jul. 8, 1988, abandoned.

[30] Foreign Application Priority Data

Jul. 11, 1987 [JP] Japan ............... 62-172067

[51] Int. Cl.$^5$ ................. A61F 2/04
[52] U.S. Cl. .................. 623/12; 623/66
[58] Field of Search ............... 673/1, 12, 66

[56] References Cited

U.S. PATENT DOCUMENTS 4,664,681  5/1987  Anazawa et al. .......... 55/158
4,708,800 11/1987  Ichikawa et al. .
4,770,852  9/1988  Takahara et al. .......... 422/48

Primary Examiner—David Isabella
Assistant Examiner—Gina M. Gualtieri
Attorney, Agent, or Firm—Sherman and Shalloway

[57] ABSTRACT

A membrane-type artificial lung adapted to perform exchange of gases between blood and a gas through a membrane by passing blood over one side of the membrane and oxygen or an oxygen-containing gas over the other side, said membrane being a hollow fiber membrane which is composed mainly of a polyolefin, has an inside diameter of 10 to 500 micrometers, a thickness of 5 to 100 micrometers, a porosity of 7 to 50% and an oxygen flux, $Q(O_2)$, of at least $1\times10^{-6}$ [$cm^3$ (STP)/($cm^2$.sec.cmHg)] and is substantially impermeable to ethanol.

8 Claims, 2 Drawing Sheets

ARTIFICIAL LUNG AND METHOD OF USING IT

This application is a continuation of application Ser. No. 07/216,547 filed Jul. 8, 1988, now abandoned.

This invention relates to a membrane-type artificial lung for adding oxygen to blood and removing carbon dioxide in extracorporeal blood circulation, and a method of using it. More specifically, this invention relates to a membrane-type artificial lung being free from plasma leakage and having high gas exchangeability in long-term use, and to a method of using it.

Artificial lungs have been studied as an auxiliary means for open heart surgery or long-term respiration aiding means. These artificial lungs perform a gas exchanging function of adding oxygen to blood and removing carbon dioxide for biological lungs, and now bubble-type artificial lungs and membrane-type artificial lungs find applications as artificial lungs for open heart surgery. Membrane-type artificial lungs have also been developed for aiding respiration.

The bubble-type artificial lungs are widely used clinically. But since they involve direct blowing of oxygen into the blood, various troubles such as hemolysis, protein denaturation, blood coagulation, occurrence of micro emboli and activation of white blood cells or complements are liable to occur. Another defect is that after use for a long period of time, the defoaming effect becomes weak, and micro bubbles are likely to get into the blood.

The membrane-type artificial lungs are adapted to permit contact between the venous blood and a gas through a membrane whereby oxygen is absorbed into the venous blood and at the same time, carbon dioxide gas is released into the gas. They are advantageous over the bubble-type artificial lungs in that they are more physiological, cause less blood damage, and have a less priming volume than the bubble-type artificial lungs. Because of these advantages, they have gradually gained acceptance clinically.

Homogeneous dense membranes composed of fluorine-containing polymers or silicone polymers have been known to be used in the membrane-type artificial lungs.

The gas exchanging ability of an artificial lung comprising a homogeneous membrane depends greatly upon the rate of dissolving of a gas in the membrane and the rate of diffusion of the gas in the membrane. The homogeneous membrane composed of a fluorine-containing polymer like polytetrafluoroethylene has excessively low dissolving and diffusion rates. The homogeneous membrane composed of a silicone polymer has the disadvantage that the silicon rubber has low mechanical strength and is difficult to form into a thin film.

As another type of the membrane-type artificial lung, a "porous membrane-type artificial lung" is known which is a hydrophobic open-cellular microporous membrane having quite a different permeation mechanism from the dissolving and diffusing mechanism. In this artificial lung, the open cells (for example, 0.08 to 4 micrometers in size) of the membrane are much larger than the gas molecules which are to permeate the membrane, and the gas molecules pass through the pores of the membrane as volumetric flows. Hence, its gas permeation velocity is about one thousand times as high as that of the homogeneous membrane, but a large amount of steam also permeates through it. Hence, the performance of the membrane is reduced because of dew formation on the membrane surface facing the gaseous phase. Furthermore, when it is used by circulating the blood for a long period of time, plasma leaks through it. Plasma leakage is presumably because protein components and the like in the plasma adhere to the membrane surface and consequently, the membrane gradually loses hydrophobicity. In the event of plasma leakage, the gas exchanging ability of the membrane is drastically reduced and sometimes it becomes useless.

To eliminate these various defects of the homogeneous membranes or porous membranes, Japanese Patent Publication No. 17052/1979 and Japanese Laid-Open Patent Publication No. 249969/1985, for example, propose a composite membrane-type artificial lung comprising a hollow fiber membrane obtained by coating or clogging the inside of the pores or the surface of a porous membrane with a silicone-type compound having especially high gas permeability among known substances. The silicone-coated or silicone-clogged porous membrane-type artificial lung has improved gas diffusibility and permeability and a higher gas exchanging ability than the homogeneous membrane-type artificial lung because theoretically, the thickness of a silicone-coated layer (clogged layer) can be reduced to a greater extent than the homogeneous membrane lung. This, however, requires a complex clogging treatment as disclosed in Japanese Laid-Open Patent Publication No. 249969/1985. Furthermore, this technique still has many technical problems to be solved and has not come into commercial acceptance. For example, it is difficult to control the thickness of the clogging layer, the strength of the membrane and pinhole formation.

Thus, the conventional homogeneous membrane-type artificial lungs have the advantage of being free from plasma leakage because they do not substantially have micropores. But since they do not permit flowing of volumetric streams, they have an inferior gas exchanging ability to the porous membrane-type artificial lungs which permit flowing of gases as volumetric streams. On the other hand, the open cellular porous membrane-type artificial lungs have a high gas exchanging ability so long as the membrane is maintained hydrophobic. However, they have the essential defect that after the lapse of 20 hours or more, their hydrophobicity is lost, and plasma leakage and the consequent drastic reduction of the gas exchanging ability occur. A further defect of the conventional composite membrane-type artificial lungs is that they become high in price owing to low productivity.

Membrane-type artificial lungs, therefore, are required to be usable for a long period of time, have equal or higher gas exchanging ability to or than the porous membrane-type artificial lungs, and be obtained at low costs as in the homogeneous membrane-type or composite membrane-type artificial lungs.

It is an object of this invention to provide a membrane-type artificial lungs which has an excellent exchanging ability of gases between blood and an oxygen-containing gas and even when used for a long period of time, leakage of plasma can be completely prevented.

The present inventors searched for a membrane which can achieve this object, and have found that a membrane composed of a polyolefin having a characteristic membrane structure has better properties than the conventional membranes for artificial lungs.

According to this invention, there is provided a membrane-type artificial lung adapted to perform exchange of gases between blood and a gas through a membrane by passing blood over one side of the membrane and oxygen or an oxygen-containing gas over the other side, said membrane being a hollow fiber membrane which is composed mainly of an olefinic polymer, has an inside diameter of 10 to 500 micrometers, a thickness of 5 to 100 micrometers, a porosity of 7 to 50% and an oxygen flux, $Q(O_2)$, of at least $1\times10^{-6}$ cm$^3$ (STP)/(cm$^2$.sec.cmHg) and is substantially impermeable to ethanol.

The invention also provides a method of using the above membrane-type artificial lung, which comprises passing an oxygen-containing gas over one side of the membrane in the artificial lung and blood over the other side of the membrane, whereby gases are exchanged between the blood and the oxygen-containing gas.

The membrane used in this invention is a semi-open cellular and closed cellular porous membrane which has fine pores (voids) in its interior but of which surface and back do not substantially communicate through pores. As the number of pores present in the interior of the membrane is larger, the flux of a gas such as oxygen or carbon dioxide becomes higher and the amount of oxygen moved to the blood or the amount of carbon dioxide removed becomes larger. If the porosity is too high, the pores are connected to one another, and pores communicating between the surface and back of the membrane (open pores) occur and cause plasma leakage. Accordingly, the membrane used in this invention should have a porosity (volume porosity) of 7 to 50%, and its preferred range is 10 to 35% although this varies slightly depending upon the method of producing the membrane.

The membrane used in this invention is a porous membrane which is substantially free from open pores and may complexly contain one or both of partial open cells and closed cells. More specifically, the membrane has a structure in which pores are open on one side (the outside surface or inside surface of the hollow fiber membrane) of the membrane but pores are not open on the other side, a structure in which pores are present in the interior of the membrane but no pores are open on its inside and outside surface, or a structure in which pores are open on both the outside and inside surfaces of the membrane but are interrupted in the interior of the membrane and do not permit communication between the surface and back of the membrane. In many cases, these structures exist together in the same membrane. The state of opening of the pores on the membrane surface can be determined visually by observing the surface of the membrane under a scanning electron microscope (SEM). The membrane used in this invention may have any one of the above structures, but preferably has a layer in which pores are not open on at least one side of the membrane. There is no particular restriction on the size of the pores, but from the standpoint of the oxygen flux, membrane strength, etc. they preferably have a diameter of 0.005 to 10 micrometers, more preferably 0.03 to 1 micrometer.

The membrane in this invention has an oxygen flux, $Q(O_2)$, of at least $1\times10^{-6}$ cm$^3$ (STP)/(cm$^2$.sec.cmHg), preferably at least $7\times10^{-6}$ cm$^3$ (STP)/(cm$^2$.sec.cmHg), more preferably $5\times10^{-5}$ to $1\times10^{-3}$ cm$^3$ (STP)/(cm$^2$.sec.cmHg). The oxygen flux is measured by a method substantially conforming to ASTM D1434. If the oxygen flux is lower than the specified limit, the speed of exchange of gases between the blood and the gas decreases, and the artificial lung of the invention is not advantageous over the homogeneous membrane-type artificial lung. Since the carbon dioxide flux of the membrane used in this invention is equal to, or higher than, its oxygen flux, a sufficient amount of carbon dioxide can be removed from the blood so long as the membrane has an oxygen flux within the above-specified range. Of course, higher oxygen fluxes are preferred. The oxygen flux of the membrane can be increased by, for example, selecting a material having a high oxygen permeability coefficient, increase the porosity of the membrane, or decreasing the thickness of the barrier layer through which the gases permeates in the polymer constituting the membrane in accordance with the dissolving-diffusion mechanism. There is naturally a limit to the maximum oxygen flux that can be achieved. But since high oxygen fluxes themselves do not cause any inconvenience, it is not necessary to set an upper limit to the oxygen flux.

If pores permitting communication between the surface and back of the membrane (open cells) exist, the oxygen flux of the membrane becomes high, but plasma undesirably leaks. The presence or absence of open cells and their number can be determined by the amount of ethanol permeated. If there is an open cell in the membrane, ethanol gets into its inside and permeates through the membrane as a liquid. For example, if 70% ethanol is forced under a pressure of 0.5 kgf/cm$^2$ into an open-cellular polypropylene membrane used in a porous membrane-type artificial lung from one side, ethanol permeates the membrane at a velocity of 1,000 to 40,000 ml/(min.m$^2$). With the membrane of this invention, the flux of ethanol is very small, and ethanol does not substantially permeate through the membrane. That the membrane is "substantially impermeable to ethanol" means that the amount of ethanol permeated is not more than 30 ml/(min.m$^2$) under the same measuring conditions. The amount of ethanol permeated (flux) through the membrane used in this invention is preferably not more than 10 ml/(min.m$^2$), more preferably not more than 2 ml/(min.m$^2$).

It is not essential in this invention to specify the position, in the membrane, of the ethanol barrier layer which is not open-cellular and is substantially impermeable to ethanol. It may exist on one or both sides of the membrane surface, or in the interior of the membrane as a single layer or a multiplicity of layers in complex shapes.

A membrane structure in which this barrier layer is formed on that side of the membrane surface which makes contact with the blood is preferred in order to prevent closing of voids by plasma or condensed moisture. In other words, it is preferred to form the ethanol barrier layer on the outside surface of the hollow fiber membrane in an exterior perfusion-type artificial lung in which the blood is passed over the outside of the hollow fiber membrane, and on the inside surface of the hollow fiber membrane in an interior perfusion-type artificial lung in which the blood is passed over the inside of the hollow fiber membrane. To decrease the thickness of the barrier layer, it is preferred to provide only one such barrier layer. Whether the barrier layer (nonporous layer) is formed on the membrane surface can be determined by observation under a scanning electron microscope.

The average thickness of the ethanol barrier layer in the entire membrane can be presumed by calculation from the actually measured gas fluxes.

Specifically, the average thickness (L) of the barrier layer is calculated from the following equation assuming that the gas which permeates through the membrane is the sum of a portion which permeates the barrier layer in the membrane as dissolution-diffusion flows and a portion which permeates through open cells connecting the surface and back of the membrane as Knudsen flows (parallel-aligned structure).

$$L = \frac{\alpha(\alpha_1 - \alpha_2)}{\alpha_1(\alpha - \alpha_2)} \times \frac{P(O_2)}{Q(O_2)} \quad (1)$$

where $\alpha = \frac{Q(O_2)}{Q(N_2)}$ [−]: the separation coefficient of the membrane $\alpha_1 = \frac{P(O_2)}{P(N_2)}$ [−]: the separation coefficient of the material polymer constituting the membrane (permeation through the barrier layer)

$\alpha_2 = \sqrt{\frac{Mw(N_2)}{Mw(O_2)}} = 0.935$ [−]: the separation coefficient of the Knudsen flows (permeation through open cells)

$P(O_2)$ [cm$^3$ (STP) · cm/(cm$^2$ · sec · cmHg)]: the oxygen permeabiltiy coefficient of the material polymer The present inventors have found that at a constant oxygen flux $Q(O_2)$, the membrane has a higher ability to add oxygen to the blood as the thickness L of the barrier layer calculated in accordance with formula (1) becomes smaller. Although the reason for it has not been elucidated in detail, it is presumed that in supplying oxygen to the blood, the contribution of that portion of oxygen which flows through the open cells is smaller than that portion which flows through the barrier layer. The barrier layer thickness of the hollow fiber membrane that can be used in this invention is not more than 10 micrometers, preferably not more than 2 micrometers, more preferably not more than 0.7 micrometer. In view of the production technology, it is extremely difficult to decrease the thickness of the barrier layer to less than 0.01 micrometer.

When $\alpha$ is less than 1 in equation (L), the error of the thickness of the barrier layer calculated in accordance with equation (1) becomes larger. In this case, the thickness may be calculated by using the measured fluxes of carbon dioxide and nitrogen instead of the measured fluxes of oxygen and nitrogen.

The characteristic feature of the membrane-type artificial lung of this invention is that a hollow fiber membrane having the characteristic structure and gas permeating characteristics is used as a gas exchanging membrane in the artificial lung. The artificial lung of this invention may be made in an extracapillary blood flow-type, an intracapillary blood flow-type or any other type. It is effective however to build the artificial lung of this invention in an extracapillary blood flow-type in order to take advantage of the characteristics of the hollow fiber membrane (the barrier layer can be formed on the outside surface of the membrane; hollow fibers of a small diameter having high performance can be produced at low cost; the thickness can be decreased for the diameter). The performance of the hollow fiber membrane can be exhibited more by tying hollow fiber membranes crosswise in a sparsely parallel-aligned pattern, and incorporating the resulting sheet in assembling the extracapillary blood flow-type artificial lung. This method can prevent channelling of the blood.

When the membrane-type artificial lung of this invention is used in an intracapillary blood flow mode, the artificial lung typically includes 1,000 to 100,000 hollow fibers with the total area of their inside surfaces being 0.1 to 7 m$^2$ and its gas exchanging portion is of a cylindrical shape with an outside diameter of not more than 25 cm and a length of not more than 30 cm.

When the membrane-type artificial lung of this invention is used in an extracapillary blood flow mode, the artificial lung typically includes 1,000 to 60,000 hollow fibers with the total area of their insides being 0.1 to 3.5 m$^2$ and its gas exchanging portion is of a cylindrical shape with an outside diameter of not more than about 20 cm and a length of not more than 30 cm.

The polymer constituting the membrane used in this invention is a polyolefin. The polyolefin has various useful characteristics. For example, it has high oxygen and carbon dioxide permeability coefficients, excellent compatibility with blood, and fabricability into a non-open cellular porous membrane. It can be formed into a film by a melting method which is not likely to leave a solvent in the membrane. Because it has high mechanical strength and form a membrane of a small thickness, a compact artificial lung device can be built by using the resulting membrane. It does not significantly contain hazardous impurities. Since it has no hygroscopicity, it is easy to handle. It has chemical resistance and is easy to sterilize. The price of the polyolefin is low. Examples of suitable polyolefins used in this invention are poly(4-methylpentene-1), polypropylene, polyethylene, polybutene-1 and copolymers of these. Of these, poly(4-methylpentene-1) is especially preferred for a variety of reasons. For example, because it has a high gas permeability coefficient, it is possible to increase the oxygen flux $Q(O_2)$ and decrease the thickness L of the barrier layer. Moreover, the barrier layer is easy to form on the membrane surface. Poly(4-methylpentene-1) has the lowest surface energy among the polyolefins exemplified above does not easily get wet by condensed water vapor on the membrane surface to decrease the gas exchanging area, and hematologically does not significantly activate complements. Accordingly, the poly(4-methylpentene-1) is a preferred material for the membrane also from this viewpoint.

The material composed mainly of the polyolefin used in this invention may be composed of at least one polyolefin as a main component and may comprise other substance. For example, it may contain a crosslinking agent or an antimicrobial agent, or may be a blend with another polymer. It is also possible to subject it to a surface treatment such as plasma treatment or such treatments as radiation crosslinking.

The membrane used in this invention may be in the form of a hollow fiber or a tube, and have an inside diameter of 10 to 500 micrometers, preferably 100 to 300 micrometers, and a thickness of 5 to 100 micrometers, preferably 10 to 40 micrometers. The membrane in accordance with this invention has a small thickness for its inside diameter as compared with a silicone homogeneous membrane. Thus, since the volume of the membrane of this invention in the entire artificial lung module is low, and the membrane has a high gas flux, the artificial lung module can be built in a compact size. Hence, the priming volume can be reduced and the artificial lung can be produced at low cost.

In the membrane of this invention, the hollow fibers are preferably used as a sheet in which the hollow fibers are aligned parallel to each other sparsely while they are tied crosswise. The sheet may be made, for example, by tying the hollow fibers with yarns or adhesive tapes in a direction perpendicular to the longitudinal axis of the hollow fibers, or by bonding the hollow fibers with yarns having an adhesive applied thereto. It should be understood that the sparsely aligned hollow fiber sheet is not limited to the specific examples given above.

The artificial lung of this invention so made is, for example, an artificial lung having an available membrane area of 0.8 m², and constructed by using hollow fiber membranes made of poly(4-methylpentene-1) and having a thickness of 27 micrometers, an outside diameter of 272 micrometers and a porosity of 18% and including a smooth barrier layer on the inside surface of the hollow fiber membranes. When in this artificial lung, blood is passed over the inside of the hollow fiber membrane and the amount of oxygen moved and the amount of carbon dioxide removed were measured at a blood temperature of 37° C. under an oxygen partial pressure of 38 mmHg and a carbon dioxide partial pressure of 45 mmHg in the blood. The amount of oxygen moved was 1.4 times as large, and the amount of carbon dioxide removed was 1.5 times as large, as those measured by using an artificial lung made by using a silicone homogeneous membrane having a thickness of 100 micrometers, an outside diameters of 400 micrometers and having the same membrane area under the same conditions as described above. Furthermore, the amount of oxygen moved and the amount of carbon dioxide removed with the artificial lungs were slightly higher than those obtained with an artificial lung using a polypropylene porous membrane having a thickness of 215 micrometers, an outside diameter of 25 micrometers and a porosity of 40%. Plasma leakage occurred in the polypropylene porous membrane but did not at all occurred in the membrane used in this invention. Furthermore, when blood was passed through the outside of the hollow fiber membrane having the hollow fibers aligned sparsely, both the amount of oxygen moved and the amount of carbon dioxide removed were 2.0 times as large as those measured when the blood was passed through the inside of the hollow fiber membrane, and in addition, the pressure drop was very small. These facts show that the artificial lung of this invention has superior performance to the conventional artificial lungs.

There is no particular limitation on the method of producing the membrane used in this invention. Generally, a melt spinning method, a jet spinning method and a dry-jet-wet spinning method are suitable, and the melt spinning method is especially suitable from the standpoint of productivity and the performance of the membrane obtained. For example, the membrane used in this invention can be produced by the methods described in Japanese Laid-Open Patent Publications Nos. 196706/1984, 229320/1984, 101206/1987, and 101227/1987. In order, however, to impart a high ability to add oxygen to blood and to prevent leakage of plasma and the ability to have resistance to degradation upon long-term use to the hollow fiber membrane, such a melt spinning method is preferably carried out under the following conditions. Specifically, the method is preferably carried out at a melting temperature of $(Tm+15)$ to $(Tm+65)$ °C. (Tm is the crystalline melting point of the polymer), a draw ratio in orientation drawing of 1.0 to 1.1, an annealing temperature of $(Tm-35)$ to $(Tm-10)$ °C., a draw ratio of 1.0 to 1.2, a draw ratio in cold drawing of 1.1 to 1.6 and a draw ratio in hot drawing of 1.3 to 2.0 for an annealing time of 2 to 30 seconds. By adjusting the conditions in each of the steps within the above ranges, the oxygen flux and porosity of the membrane, the thickness of the barrier layer, etc. can be adjusted so as to conform to the use of the membrane as an artificial lung.

A porous membrane having a smooth barrier layer in at least one side of a hollow fiber membrane can be produced by melt-extruding a polyolefin having a maximum degree of crystallinity of at least 20% into hollow fibers; as required, orienting and drawing the hollow fibers; heat annealing them; and then cold drawing the hollow fibers and heat setting them. Presumably because the pores in the membrane are long in a direction perpendicular to the membrane surface owing to the mechanism of membrane formation, the membrane produced by this method has a relatively low porosity and yet a sufficiently high oxygen flux and is substantially impermeable to alcohol. Furthermore, it has high mechanical strength and its thickness can be adjusted to a small one. Furthermore, since no solvent is used, toxic substances are not dissolved out from the membrane. Another feature is that the productivity of producing the membrane used in this invention is high, and it can be produced at a much lower cost than the composite membrane.

When compared with an artificial lung made by using a conventional homogeneous membrane, the artificial lung of this invention has a high performance. Moreover, while the composite membrane-type artificial lung requires two steps of forming a porous membrane and then forming it into a composite membrane for its production, the membrane used in the artificial lung of this invention can be formed in one step. In addition, the production of the composite membrane usually uses a solvent, and this raises a problem in regard to the working environment, atmospheric pollution, the remaining of the solvent and the drying time. The membrane used in this invention can be produced by the melt spinning method which is free from these problems. The present invention has the advantage that a smooth barrier layer can be easily formed on the inside surface, outside surface or both of the hollow fiber membrane unlike the composite membrane, and a membrane suited for a particular purpose of use can be supplied.

The following examples illustrate the present invention more specifically partly with reference to the accompanying drawings.

EXAMPLE 1

Poly(4-methylpentene-1) having a melt index (measured by ASTM D1238) of 26 was melt-spun by using annular nozzles (diameter 6 mm) for hollow fibers at a spinning temperature of 290° C., a take-up speed of 300 m/min. and a draft ratio of 270 to form hollow fibers having an outside diameter of 343 micrometers and a thickness of 34 micrometers. During the spinning, the fibers were cooled by air at a temperature of 25° C. at a speed of 1.5 m/sec. to a region 3 to 35 cm below the nozzles. The hollow fibers were continuously oriented and drawn at a temperature of 35° C. and a draw ratio of 1.05 by a roller system, then annealed at a draw ratio of 1.3 by introducing them into a hot air circulating-type constant temperature vessel at 200° C. and allowing them to stay there for 5 seconds, subsequently cold-drawn at 35° C. and a draw ratio of 1.2, hot-drawn at 150° C. and a draw ratio of 1.2, and heat-set at 200° C. and a draw ratio of 0.9. The hollow fiber membranes obtained had an outside diameter of 272 micrometers and a thickness of 27 micrometers. The inside and outside surfaces of the membranes were observed by SEM (12,000 X). The inside surface was smooth and without any pore observed. Many micropores having a size of about 0.1 micrometer were observed on the outside surface.

Figure 1:
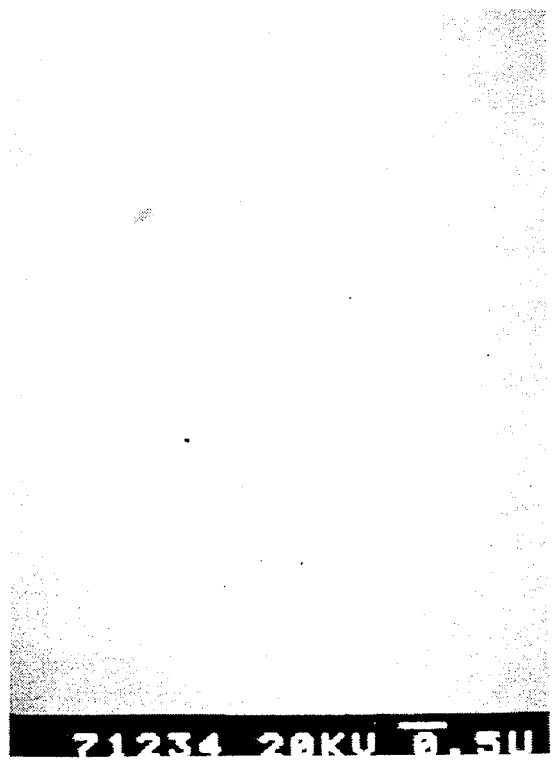
FIG. 1 is a scanning electron micrograph showing the microstructure of the inside surface of the hollow fiber obtained in Example 1 (in which the pores are not observed)
Figure 2:
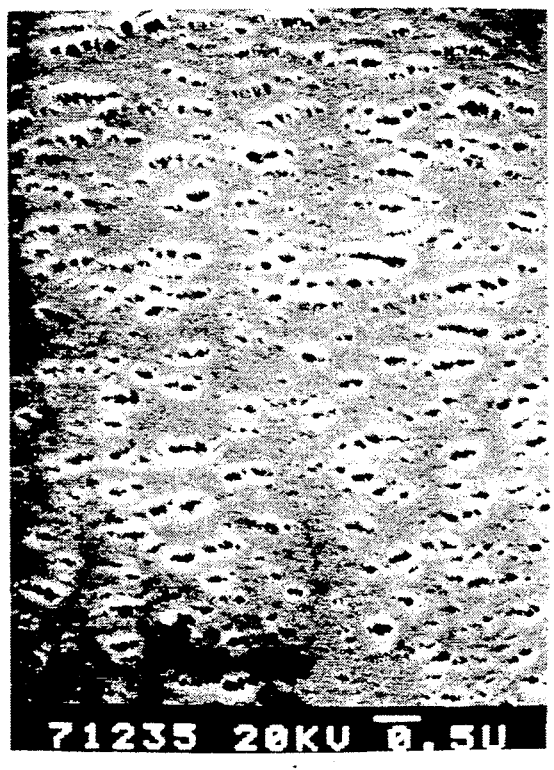
FIG. 2 is a scanning electron micrograph showing the outside surface of the hollow fibers obtained in Example 1 (the pores having a size of about 0.2 micrometer is observed)
Figure 3:
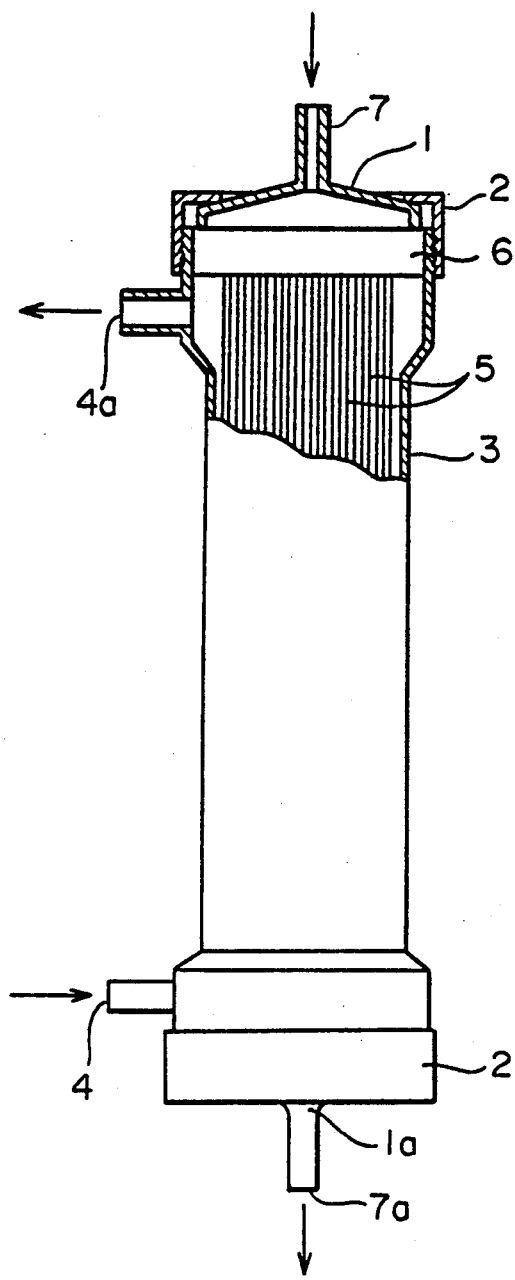
FIG. 3 is a vertical sectional view of the artificial lung of this invention.

The hollow fiber membrane (0.5 g) was cut to a length of about 10 mm, and filled in a pycnometer. The pycnometer was evacuated by a vacuum pump to $1 \times 10^{-2}$ torr or below, mercury was filled into the pycnometer, and the weight of the pycnometer was measured. The volume of the hollow fiber membrane at 25° C. was 0.72 cm$^3$. The porosity of the hollow fiber membrane, calculated by using the true specific gravity of the poly(4-methylpentene-1) which is 0.82, was 18%. The hollow fiber membrane was sealed in a glass tube, and its gas fluxes were measured at 25° C. in accordance with ASTM D1434 (pressure method). The results were as follows:

$Q(O_2) = 4.5 \times 10^{-5}$ cm$^3$ (STP)/(cm$^2$.sec.cmHg)
$Q(CO_2) = 3.4 \times 10^{-5}$ cm$^3$ (STP)/(cm$^2$.sec.cmHg)
$\alpha(O_2/N_2) = 1.2$
L (barrier layer) = 1.3 micrometers An example of an artificial lung using the hollow fiber membranes is shown in FIG. 3.

The artificial lung is comprised of a housing 3, hollow fiber membranes 5 and end walls 6 of a polymer provided at both end portions of the housing 3. For example, about 8,000 hollow fiber membranes 5 are aligned longitudinally in spaced-apart relationship, and both ends of the hollow fiber membranes 5, in the open state, are fixed to the inside wall of the housing 3 by means of the end walls 6. A gas inlet 4 and a gas outlet 4a are provided in the housing, and caps 1 and 1a are put over the outside surface of the end walls 6 respectively by rings 2. A blood inlet 7 and a blood outlet 7a are disposed respectively in the caps 1 and 1a.

70% Ethanol which is a liquid for wetting the membranes was allowed to flow at a rate of 200 cm$^3$/min. through the hollow portions of the artificial lung (available membrane area 0.8 m$^2$), and a pressure difference between the inside and outside of the membrane of 0.5 kgf/cm$^2$. The amount of 70% ethanol permeated was 0.8 cm$^3$/(min.m$^2$). This shows that the membranes have a barrier layer substantially impermeable to the liquid.

The gas exchanging ability of the artificial lung was examined by the following procedure. Using fresh heparinized bovine blood, a standard venous blood having a temperature of 36° C., a hemoglobin content of 12.1 g/dl, an oxygen saturation degree of 65% and a carbon dioxide partial pressure of 45 mmHg was prepared. The standard venous blood was passed through the hollow portions of the hollow fiber membranes in the artificial lungs, and 100% oxygen was passed at a rate of 1 liter/mon. over the outside surfaces of the hollow fiber membranes. The maximum blood flow (MBF) which maintained the oxygen saturation degree on the outlet side of the artificial lung at 95% or more was determined.

Furthermore, using a hybrid adult dog, an extracorporeal circulation was carried out for 24 hours through the vein, the artificial lung and the artery, and the amount of plasma which leaked was measured. The results in Table 1 show that the artificial lung of this invention is free from plasma leakage and has a sufficient gas exchanging ability for practical purposes.

EXAMPLE 2

Hollow fiber membranes were produced in the same way as in Example 1 except that the spinning temperature was changed to 300° C., and the draw ratio in the orientation and drawing was changed to 1.2. Observation under SEM showed that pores having a size above the resolving power (about 30 Å) of SEM did not exist on the inside and outside surfaces of the hollow fiber membranes. The membranes had an outside diameter of 250 micrometers, a thickness of 25 micrometers and a porosity of 11%. The membranes had an oxygen flux $Q(O_2)$ of $8 \times 10^{-6}$ cm$^3$ (STP)/(cm$^2$.sec.cmHg), an $\alpha$ of 4.1, and L of 2.5 micrometers and a $Q(CO_2)$ of $3.9 \times 10^{-5}$ cm$^3$ (STP)/(cm$^2$.sec.cmHg).

An artificial lung built as in Example 1 using the hollow fiber membranes showed a 70% ethanol permeating amount of 0.15 cm$^3$/(min.m$^2$). The MBF and amount of plasma leakage of the artificial lung were measured, and the results are shown in Table 1.

EXAMPLE 3

Polypropylene having a melt index (measured by ASTM D1238) of 3.5 was melt-spun by using annular nozzles (diameter 6 mm) for hollow fibers at a spinning temperature of 250° C., a take-up speed of 300 m/min. and a draft ratio of 270 to form hollow fibers having an outside diameter of 345 micrometers and a thickness of 34 micrometers. During the spinning, the fibers were cooled by air at a temperature of 8° C. at a speed of 1.5 m/sec. to a region 3 to 35 cm below the nozzles. The hollow fibers were continuously oriented and drawn at a draw ratio of 1.2 by a roller system, then annealed at a temperature of 35° C. and a draw ratio of 1.3 by introducing them into a hot air circulating-type constant temperature vessel at 140° C. and allowing them to stay there for 5 seconds, subsequently cold-drawn at 10° C. and a draw ratio of 1.2, hot-drawn at 140° C. and a draw ratio of 1.2, and heat-set at 140° C. and a draw ratio of 0.9. The hollow fiber membranes obtained had an outside diameter of 257 micrometers, an inside diameter of 205 micrometers and a thickness of 26 micrometers. The inside and outside surfaces of the membranes were observed by SEM (12,000 X). The inside surface hardly contained pores, and many micropores having a size of about 0.1 micrometer were observed on the outside surface.

The hollow fiber membranes had a porosity of 31%, an oxygen flux $Q(O_2)$ of $3.4\times0^{-4}$ cm$^3$ (STP)/(cm$^2$.sec.cmHg), an $\alpha$ of 0.94, and L of 1.6 micrometers and a $Q(O_2)$ of $2.92\times10^{-4}$ cm$^3$ (STP)/(cm$^2$.sec.cmHg). L was calculated by using $Q(CO_2)$ because the use of $Q(O_2)$ would produce a large error.

An artificial lung built as in Example 1 using the hollow fiber membranes showed a 70% ethanol permeating amount of 22 cm$^3$/(min.m$^2$). The MBF and the amount of plasma leakage of the artificial lung were measured, and the results are shown in Table 1.

EXAMPLE 4

Polyethylene having a melt index (measured by ASTM D1238) of 1.8 and a density of 0.96 was melt-spun by using annular nozzles (diameter 10 mm) for hollow fibers at a spinning temperature of 230° C., a draft ratio of 700, a cooling air temperature of 12° C. and a cooling air speed of 1.5 m/sec. The hollow fibers were continuously oriented and drawn at a temperature of 20° C. and a draw ratio of 1.2 by a roller system, then annealed at a temperature of 80° C. and a draw ratio of 1.2 with a residence time of 5 seconds, cold-drawn at 20° C. and a draw ratio of 1.3, hot-drawn at 60° C. and a draw ratio of 1.2, and heat-set at 80° C. and a draw ratio of 1.0. The hollow fiber membranes obtained had an inside diameter of 200 micrometers and a thickness of 24 micrometers. Observation under SEM showed that no pores existed on both the inside and outside surfaces of the membranes, and the porous layer with a pore size of about 1 micrometer existed between the inside and outside surfaces in the cross section of the membranes. The hollow fiber membranes had a porosity of 25%, an oxygen flux $Q(O_2)$ of $1.5\times10^{-4}$ cm$^3$ (STP)/(cm$^2$.sec.cmHg), an $\alpha$ of 0.95, an L of 0.6 micrometer and a $Q(CO_2)$ of $1.33\times10^{-4}$ cm$^3$ (STP)/(cm$^2$.sec cmHg). L was calculated as in Example 3.

An artificial lung was built as in Example 1 using the hollow fiber membranes. It had a 70% ethanol flux 14.8 cm$^3$/(min.m$^2$). The membranes in this example, too, had an ethanol barrier layer substantially impermeable to liquids. The gas exchanging ability and the amount of plasma leakage are shown in Table 1.

COMPARATIVE EXAMPLE 1

An artificial lung having an effective area of 0.8 m$^2$ was built in the same way as in Example 1 except that porous polypropylene hollow fiber membranes without a barrier layer having an inside diameter of 200 micrometers, a thickness of 30 micrometers, a porosity of 40% and a maximum pore diameter of 0.6 micrometer were used instead of the hollow fiber membranes used in Example 1. The MBF and plasma leakage amount of the membranes were measured, and the results are shown in Table 1.

COMPARATIVE EXAMPLE 2

An artificial lung having an effective area of 0.8 m$^2$ was built in the same way as in Example 1 except that silicone rubber hollow fiber membranes having an inside diameter of 200 micrometers and a thickness of 100 micrometers were used instead of the hollow fiber membranes used in Example 1. The MBF and plasma leakage amount of the membranes were measured, and the results are shown in Table 1.

TABLE 1

| Run | Maximum blood flow (cm$^3$/min.) | Cumulative amount of plasma that flowed (cm$^3$) |
|---|---|---|
| Example 1 | 1010 | 0 |
| Example 2 | 900 | 0 |
| Example 3 | 770 | 3.3 |
| Example 4 | 820 | 1.8 |
| Comparative Example 1 | 960 | above 100 |
| Comparative Example 2 | 700 | 0 |

EXAMPLE 5

Hollow fiber membranes having an outside diameter of 255 micrometers and a thickness of 26 micrometers were produced under the same conditions as in Example 1 except that the spinning draft ratio was changed to 350, the annealing was carried out at 220° C. and a draw ratio of 1.1 and the hot draw ratio was changed to 1.4. Observation under SEM showed that pores having a size of about 0.1 micrometer existed on the about $50\times10^9$/cm$^2$, and only about 1/50 of the pores existed on the outside surface. The fiber membranes had a $Q(O_2)$ of $3\times10^{-4}$ cm$^3$ (STP)/(cm$^2$.sec cmHg), an $\alpha$ of 1.02 and a $Q(CO_2)$ of $3.4\times10^{-4}$ cm$^3$ (STP)/(cm$^2$.sec.cmHg). The thickness of the barrier layer calculated from equation (1) given hereinabove and the characteristic values of poly(4-methylpentene-1)[$P(O_2)=2.0\times100^{-9}$ cm$^3$ (STP)/(cm$^2$.sec.cmHg), $\alpha=4.1$] was 0.6 micrometer. The porosity of the hollow fiber membrane measured as in Example 1 was 23.5%.

Figure 4:
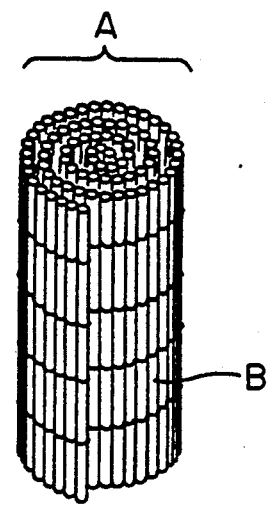
FIG. 4 is a view showing the hollow fiber membrane sheet having the hollow fibers aligned sparsely which was used in Examples 5 to 7.

The hollow fiber membranes were tied crosswise with yarns in a sparsely and longitudinally aligned pattern to form a sheet having this set-up. The sheet is rolled up to form a bundle A of the hollow fibers B as shown in FIG. 4. The bundle was placed in a cylindrical housing 3 as in the case of the hollow fiber membranes 5 shown in FIG. 3, and a membrane-type artificial lung having a membrane area of 2.5 m$^2$ was built. The artificial lung had a 70% ethanol flux of 2.1 cm$^3$/(min.m$^2$). When the same bovine blood as used in Example 1 was allowed to flow over the outside surfaces of the hollow fiber membranes and 100% oxygen was allowed to flow over the inside surfaces of the hollow fiber membranes at a flow rate of 1 liter/min., the maximum amount of blood flow at which the oxygen saturation degree on the exit side of the artificial lung was maintained at 95% or more was 2950 cm$^3$/(min.m$^2$). Even when this artificial lung was used continuously for 1 week, plasma did not leak at all, and there was hardly any decrease in gas exchanging ability with time. After use, the artificial lung was washed with physiological saline to remove the blood, adhesion of the blood clots to the outside surface of the hollow fibers was very little.

EXAMPLE 6

An exterior perfusion-type artificial lung having an available membrane area of 2.0 m$^2$ was built and evaluated in the same way as in Example 5 except that the same hollow fiber membranes as in Example 5 were tied with slender adhesive tapes in a sparsely aligned pattern. The MBF of the artificial lung was 2200 cm$^3$/(min.m$^2$).

EXAMPLE 7

Hollow fiber membranes were produced as in Example 5 except that the annealing time was changed to 10 seconds, the cold draw ratio was changed to 1.3 and the hot draw ratio was changed to 1.8.

The hollow fiber membranes obtained had a $Q(O_2)$ of $3.0 \times 10^{-4}$ cm$^3$ (STP)/(cm$^3$.sec cmHg), an $\alpha$ of 0.98, an L of 1.1 micrometers, a $Q(CO_2)$ of $3.0 \times 10^{-4}$ cm$^3$ (STP)/(cm$^3$.sec.cmHg), and a porosity of 27%.

Using the hollow fiber membranes, an artificial lung was built. It had an ethanol permeating rate of 3.9 cm$^3$/(min.m$^2$) and an MBF of 2500 cm$^3$/(min.m$^2$).

We claim:

1. A hollow fiber artificial lung adapted to perform exchange of gases between blood and a gas through a hollow fiber membrane by passing blood over one side of the membrane and oxygen or an oxygen-containing gas over the other side, said hollow fiber membrane consisting essentially of a polyolefin, said hollow fiber membrane having:
    an inside diameter of 10 to 500 micrometers;
    a thickness of 5 to 100 micrometers;
    a porosity of 7 to 50%,
    an oxygen flux, $Q(O_2)$, of at least $1 \times 10^{-6}$,
    a barrier layer having an average thickness of not more than 2 micrometers as calculated from oxygen flux $Q(O_2)$ and nitrogen flux $Q(N_2)$, and
    an ethanol flux across the hollow fiber membrane of not more than 30 ml/(min.m$^2$).

2. The hollow fiber artificial lung of claim 1 in which the polyolefin is poly(4-methylpentene-1).

3. The hollow fiber artificial lung of claim 1 in which the hollow fiber membrane has an oxygen flux, $Q(O_2)$, at 25° C. of at least $7 \times 10^{-6}$ cm$^3$ (STP)/(cm$^2$.sec.cmHg).

4. The hollow fiber artificial lung of claim 1 wherein the hollow fiber membrane has a porosity of 10 to 35%.

5. The hollow fiber artificial lung of claim 1 in which the hollow fiber membrane has an inside diameter of 100 to 300 micrometers and a thickness of 5 to 100 micrometers.

6. The hollow fiber artificial lung of claim 1 in which the hollow fiber membrane is an assembly of hollow fibers sparsely aligned lengthwise and tied together across by yarns or tapes disposed perpendicular to said lengthwise hollow fibers.

7. A method of exchanging gases between blood and an oxygen-containing gas comprising:
    providing a hollow fiber artificial lung adapted to perform exchange of gases between blood and a gas through a hollow fiber membrane by passing blood over one side of the membrane and oxygen or an oxygen-containing gas over the other side, said hollow fiber membrane consisting essentially of a polyolefin, said hollow fiber membrane having:
        an inside diameter of 10 to 500 micrometers;
        a thickness of 5 to 100 micrometers;
        a porosity of 7 to 50%,
        an oxygen flux, $Q(O_2)$, of at least $1 \times 10^{-6}$, and
        a barrier layer having an average thickness of not more than 2 micrometers as calculated from oxygen flux $Q(O_2)$ and nitrogen flux $Q(N_2)$ which is substantially impermeable to ethanol; and
    passing an oxygen-containing gas over an inside surface of the membrane and blood over an outside surface, thereby performing exchange of gases between said blood and said oxygen-containing gas.

8. A method of exchanging gases between blood and an oxygen-containing gas comprising:
    providing a hollow fiber artificial lung adapted to perform exchange of gases between blood and a gas through a hollow fiber membrane by passing blood over one side of the membrane and oxygen or an oxygen-containing gas over the other side, said hollow fiber membrane consisting essentially of a polyolefin, said hollow fiber membrane having:
        an inside diameter of 10 to 500 micrometers;
        a thickness of 5 to 100 micrometers;
        a porosity of 7 to 50%,
        an oxygen flux, $Q(O_2)$, of at least $1 \times 10^{-6}$, and
        a barrier layer having an average thickness of not more than 2 micrometers as calculated from oxygen flux $Q(O_2)$ and nitrogen flux $Q(N_2)$ which is substantially impermeable to ethanol; and
    passing an oxygen-containing gas over an outside surface of the membrane and blood over an inside surface, thereby performing exchange of gases between said blood and said oxygen-containing gas.

* * * * *